US009599562B2

(12) United States Patent
Englund (10) Patent No.: US 9,599,562 B2
(45) Date of Patent: Mar. 21, 2017

(54) CONJUGATES OF NANO-DIAMOND AND MAGNETIC OR METALLIC PARTICLES

(71) Applicant: THE TRUSTEES OF COLUMBIA UNIVERSITY IN THE CITY OF NEW YORK, New York, NY (US)

(72) Inventor: Dirk R. Englund, New York, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 0 days.

(21) Appl. No.: 14/952,216

(22) Filed: Nov. 25, 2015

(65) Prior Publication Data

US 2016/0077004 A1 Mar. 17, 2016

Related U.S. Application Data

(63) Continuation of application No. 14/150,412, filed on Jan. 8, 2014, now Pat. No. 9,222,887, which is a
(Continued)

(51) Int. Cl.
*G01N 21/64* (2006.01)
*G01N 33/487* (2006.01)
(Continued)

(52) U.S. Cl.
CPC ........... *G01N 21/64* (2013.01); *G01N 21/643* (2013.01); *G01N 21/6428* (2013.01);
(Continued)

(58) Field of Classification Search
CPC .... G01N 21/64; G01N 21/6458; G01N 22/00; G01N 33/54326
See application file for complete search history.

(56) References Cited

U.S. PATENT DOCUMENTS 3,694,656 A    9/1972  Henning
5,037,376 A    8/1991  Richmond et al.
(Continued)

FOREIGN PATENT DOCUMENTS

WO    WO 94/06152 A1     3/1994
WO    WO 2008/128051 A2  10/2008
(Continued)

OTHER PUBLICATIONS

Petráková V., "Optical Detection of Charged Biomolecules: Towards Novel Drug Delivery Systems," Acta Polytechnica, 51(5):89-93 (2011) Retrieved from the Internet: URL:https://ojs.cvut.cz/ojs/index.php/ap/article/view/1450/1282 [retrieved on Apr. 27, 2016].
(Continued)

*Primary Examiner* — Marcus Taningco
(74) *Attorney, Agent, or Firm* — Baker Botts L.L.P.

(57) ABSTRACT

Techniques for imaging a characteristic of a sample with a plurality of conjugates of diamond-metallic nanoparticles having a nitrogen vacancy center. The plurality of conjugates can be exposed to a sample and the nitrogen vacancy centers can be optically pumped. One or more microwave pulses can be applied to the nitrogen vacancy center, and a fluorescent response can be detected.

19 Claims, 8 Drawing Sheets

Related U.S. Application Data continuation of application No. PCT/US2012/048830, filed on Jul. 30, 2012.

(60) Provisional application No. 61/513,830, filed on Aug. 1, 2011, provisional application No. 61/549,046, filed on Oct. 19, 2011, provisional application No. 61/562,551, filed on Nov. 22, 2011, provisional application No. 61/591,570, filed on Jan. 27, 2012, provisional application No. 61/624,647, filed on Apr. 16, 2012.

(51) Int. Cl.
*G01N 33/58* (2006.01)
*G01N 33/543* (2006.01)
*B82Y 15/00* (2011.01)
*G01N 22/00* (2006.01)

(52) U.S. Cl.
CPC ... *G01N 21/6458* (2013.01); *G01N 33/48728* (2013.01); *G01N 33/54326* (2013.01); *G01N 33/585* (2013.01); *G01N 33/587* (2013.01); *B82Y 15/00* (2013.01); *G01N 22/00* (2013.01)

(56) References Cited

U.S. PATENT DOCUMENTS

| | | |
|---|---|---|
| 5,173,761 A | 12/1992 | Dreifus et al. |
| 5,307,146 A | 4/1994 | Porter et al. |
| 7,030,704 B2 | 4/2006 | White |
| 7,166,463 B2 | 1/2007 | Karpen et al. |
| 7,190,993 B2 | 3/2007 | Sharma et al. |
| 7,196,782 B2 | 3/2007 | Fielden et al. |
| 7,619,485 B2 | 11/2009 | DeNatale et al. |
| 7,655,376 B2 | 2/2010 | Anderson et al. |
| 7,778,296 B1 | 8/2010 | Vuckovic et al. |
| 7,869,708 B2 | 1/2011 | Evangelides, Jr. et al. |
| 8,110,898 B2 | 2/2012 | Lewis et al. |
| 9,222,887 B2 | 12/2015 | Englund |
| 2003/0052080 A1 | 3/2003 | Baik et al. |
| 2004/0079280 A1 | 4/2004 | Lee et al. |
| 2004/0213534 A9 | 10/2004 | Matsuura et al. |
| 2005/0088248 A1 | 4/2005 | White |
| 2005/0118349 A1 | 6/2005 | Whitehead et al. |
| 2005/0152429 A1 | 7/2005 | Scherer |
| 2006/0134600 A1 | 6/2006 | Fuhr et al. |
| 2006/0241236 A1 | 10/2006 | Kuznetsov et al. |
| 2006/0265039 A1 | 11/2006 | Bartic et al. |
| 2007/0048731 A1 | 3/2007 | Colicos et al. |
| 2007/0126312 A1 | 6/2007 | Sung |
| 2007/0216424 A1 | 9/2007 | Sieh et al. |
| 2008/0096308 A1 | 4/2008 | Santori et al. |
| 2008/0299565 A1 | 12/2008 | Schneider et al. |
| 2008/0319290 A1 | 12/2008 | Mao et al. |
| 2009/0115029 A1 | 5/2009 | Koyama et al. |
| 2009/0140275 A1 | 6/2009 | Santori et al. |
| 2009/0171233 A1 | 7/2009 | Lanfermann et al. |
| 2009/0233445 A1 | 9/2009 | Lee et al. |
| 2010/0016732 A1 | 1/2010 | Wells et al. |
| 2010/0084634 A1 | 4/2010 | Gamo et al. |
| 2010/0135890 A1* | 6/2010 | Boudou ............... C01B 31/065 423/384 |
| 2010/0140562 A1 | 6/2010 | Shenderova et al. |
| 2010/0181534 A1 | 7/2010 | Shenderova et al. |
| 2010/0233820 A1 | 9/2010 | Pantazis et al. |
| 2010/0298600 A1 | 11/2010 | Lee |
| 2010/0305309 A1 | 12/2010 | Ho et al. |
| 2010/0315079 A1 | 12/2010 | Lukin et al. |
| 2010/0320475 A1 | 12/2010 | Speck et al. |
| 2010/0328299 A1 | 12/2010 | Yamazaki et al. |
| 2011/0062957 A1 | 3/2011 | Fu et al. |
| 2011/0120890 A1 | 5/2011 | MacPherson et al. |
| 2011/0163291 A1 | 7/2011 | Scarsbrook et al. |
| 2011/0177008 A1 | 7/2011 | Manus et al. |
| 2011/0309265 A1 | 12/2011 | Babinec et al. |
| 2012/0000415 A1 | 1/2012 | D'Evelyn et al. |
| 2012/0019242 A1 | 1/2012 | Hollenberg et al. |
| 2013/0334170 A1 | 12/2013 | Englund et al. |
| 2014/0100472 A1 | 4/2014 | Englund et al. |
| 2014/0191139 A1 | 7/2014 | Englund et al. |
| 2014/0247094 A1 | 9/2014 | Englund et al. |

FOREIGN PATENT DOCUMENTS

| | | |
|---|---|---|
| WO | WO 2010/051580 A1 | 5/2010 |
| WO | WO 2011/102474 A1 | 8/2011 |
| WO | WO 2012/034924 A1 | 3/2012 |
| WO | WO 2013/066446 A1 | 5/2013 |

OTHER PUBLICATIONS

Petráková V. et al., "Luminescence of Nanodiamond Driven by Atomic Functionalization: Towards Novel Detection Principles," Advanced Functional Materials, 22(4):812-819 (2012).

Petráková V., "Interactions of nitrogen-vacancy centers with charged surfaces of functionalized nanodiamond particles for the detection of cellular processes," Apr. 17, 2013 Retrieved from the Internet on Apr. 27, 2016: URL: http://www.fbmi.cvut.cz/files/nodes/5223/public/Disertace Petrakova.pdf.

Supplementary European Search Report dated May 24, 2016 in EP Application No. 13805034.

U.S. Appl. No. 14/227,076, filed Mar. 27, 2014.

U.S. Appl. No. 13/973,499, Jan. 15, 2016 Non-Final Office Action.

U.S. Appl. No. 13/973,499, Dec. 7, 2015 Amendment and Request for Continued Examination (RCE).

U.S. Appl. No. 13/973,499, Jun. 17, 2015 Final Office Action.

U.S. Appl. No. 13/973,499, Apr. 7, 2015 Response to Non-Final Office Action.

U.S. Appl. No. 13/973,499, Oct. 8, 2014 Non-Final Office Action.

U.S. Appl. No. 13/973,499, Sep. 15, 2014 Response to Restriction Requirement.

U.S. Appl. No. 13/973,499, Jul. 30, 2014 Restriction Requirement Filed.

U.S. Appl. No. 14/104,931, Sep. 10, 2015 Non-Final Office Action.

U.S. Appl. No. 14/150,412, Nov. 24, 2015 Issue Fee Payment.

U.S. Appl. No. 14/150,412, Aug. 28, 2015 Notice of Allowance.

U.S. Appl. No. 14/150,412, Jun. 2, 2015 Response to Non-Final Office Action.

U.S. Appl. No. 14/150,412, Jan. 2, 2015 Non-Final Office Action.

U.S. Appl. No. 14/208,198, Feb. 12, 2016 Notice of Allowance.

U.S. Appl. No. 14/208,198, Dec. 11, 2015 Response to Non-Final Office Action.

U.S. Appl. No. 14/208,198, Dec. 8, 2015 Applicant Initiated Interview Summary.

U.S. Appl. No. 14/208,198, Sep. 11, 2015 Non-Final Office Action.

Aichele et al., "Assembly of Fundamental Photonic Elements from Single Nanodiamonds", 23rd Annual Meeting of the IEEE Photonics Society, Denver, CO, pp. 142-143 (2010).

Balasubramanian, et al., "Nanoscale imaging manetometry with diamond spins under ambient conditions", *Nature*, vol. 455, No. 7213, Oct. 2, 2008, pp. 648-651.

Behr, D. et al., "Lift-off technique of homoepitaxial CVD diamond films by deep implantation and selective etching", Diamond and Related Materials, Elsevier Science Publishers, Amsterdam, NL, vol. 6, No. 5-7, Apr. 1, 1997, pp. 654-657.

Boudou et al., "High Yield Fabrication of Fluorescent Nanodiamonds", Nanotechnology, 20:235602 (11 pages) (2009).

Bradac et al., "Observation and Control of Blinking Nitrogen-Vacancy Centres in Discrete Nanodiamonds", Nature Nanotechnology, 5:345-349 (2010).

Catledge et al., "Strong Narrow-Band luminescence from Silicon-Vacancy Color Centers in Spatially Localized Sub-10 nm Nanodiamond", Advanced Science Letters. 4(2):512-515 (2011).

Chang et al., "Mass Production and Dynamic Imaging of Flourescent Nanodiamonds", Nature Nanotechnology, 3:284-287 (2008).

(56) References Cited

OTHER PUBLICATIONS

Cheung et al., "Implantable Microscale Neural Interfaces", Biomed Microdevices, 9:923-938 (2007).
DeNatale et al., "Compact, Low-Power Chip-Scale Atomic Clock", Position, Location and Navigation Symposium 2008 IEEE, pp. 67-70 (2008).
Draganski et al., "On the Opto-Electrical Properties of Ion-Implanted Single-Crystal Diamond in the Visible and Near-Visible Regime", RMIT University, Mar. 2011, pp. 1-277 [retrieved on Jan. 10, 2012] Retrieved from the internet: URL:http://researchbank.rmit.edu.au/eserv/rmit:160121/Draganski.pdf☐.
Englund et al., "Deterministic Coupling of a Single Nitrogen Vacancy Center to a Photonic Crystal Cavity", Nano Letters, 10:3922-3926 (2010).
EP Search Report mailed May 8, 2015 in EP Patent Application No. 12 84 2617.
European Extended Search Report dated Jan. 23, 2015 in EP Application No. 12752171.
Fu et al., "Characterization and Application of Single Fluorescent Nanodiamonds as Cellular Biomarkers", PNAS, 104(3):727-732 (2007).
Han et al., "Three-Dimensional Stimulate Emission Depletion Microscopy of Nitrogen-Vacancy Centers in Diamond Using Continuous-Wave Light", Nano Letters, 9(9):3323-3329 (2009).
Hunn, J.D. et al., "Ion Beam and Laser-Assisted Micromachining of Single-Crystal Diamond", Solid State Technology, Pennwell Corporation, Tulsa, OK, US, vol. 37, No. 12, Dec. 1, 1994, pp. 57-60.
International Search Report and Written Opinion for PCT/US12/042255, dated Sep. 14, 2012.
International Search Report and Written Opinion for PCT/US12/048830, dated Apr. 5, 2013.
International Search Report and Written Opinion for PCT/US12/055555, dated Jan. 23, 2013.
International Search Report and Written Opinion for PCT/US12/060735, dated Jan. 7, 2013.
International Search Report and Written Opinion for PCT/US12/27235, dated Jun. 13, 2012.
International Search Report and Written Opinion for PCT/US13/045631, dated Nov. 14, 2013.
International Search Report and Written Opinion for PCT/US13/045795, dated Nov. 14, 2013.
International Search Report and Written Opinion for PCT/US14/020565, dated Jun. 23, 2014.
Liu et al., "Plasmon-Enhanced Photoluminescence from Bioconjugated Gold Nanoparticle and Nanodiamond Assembly", Applied Physics Letters, 98:153702-153705 (2011).
Maletinsky et al. "A Robust Scanning Diamond Sensor for Nanoscale Imaging with Single Nitrogen-Vacancy Centres", Nature Nanotechnology, 7(5):320-324 (2012).
Manson et al., "Nitrogen-Vacancy Center in Diamond: Model of the Electronic Structure and Associated Dynamics", Physical Review B, 74:104303 (11 pages) (2006).
Manus, et al., "Gd(III)- Nanodiamond Conjugates for MRI Contrast Enhancement", Nano Letters, vol. 10, No. 2, Feb. 10, 2010, pp. 484-489.
McGuinness, et al., "Quantum measurement and orientation tracking of fluorescent nanodiamonds inside living cells", *Nature Nanotechnology*, vol. 6, No. 6, May 8, 2011, pp. 358-363.
Neumann P., et al., "Excited-state spectroscopy of single NV defects in diamond using optically detected magnetic resonance", New Journal of Physics, Institute of Physics Publishing, Bristol, GB, vol. 11, No. 1, 2009, p. 13017-1 to 13017-10, XP020154302.
Qing et al., "Nanowire transistor arrays for mapping neural circuits in acute brain slices", PNAS, 107(5):1882-1887 (2010).
Schietinger et al., "Plasmon-Enhanced Single Photon Emission from a Nanoassembled Metal-Diamond Hybrid Structure at Room Temperature", Nano Letters, 9(4):1694-1698 (2009).
Seker et al., "The fabrication of low-impendance nanoporous gold multiple-electrode arrays for neural electrophysiology studies", Nanotechnology, 21(12):125504 (13 pages) (2010).
Shahriar "(QC Theme) Type-Two Quantum Computing in PBG-Based Cavities for Efficient Simulation of lattice Gas Dynamics", Northwestern University. (62 pages) Final Report Apr. 26, 2008.
Smirnov et al. "Aligned Diamond Nano-Wires: Fabrication and Characterization for Advanced Applications in Bio-and Electrochemistry", Diamond and Related Materials 2009 [retrieved on Jun. 3, 2014). Retrieved from the internet: <URL: http://www.soft-hummingbird.com/Proggis/PTD/[2010)%20-%20Smirnov"/o20-%20Diamond%20Nanowires%20(drrn).pdf> entire document.
Steinert S., et al., "High sensitivity magnetic imaging using an array of spins in diamond", Review of Scientific Instruments, AIP, Melville, NY, US, vol. 81, No. 4, Apr. 23, 2010, pp. 43705-1 to 43705-5.
Supplementary European Search Report mailed Jun. 22, 2015 in EP Application No. 12846188.
Tisler, Julia, et al., "Highly Efficient FRET from a Single Nitrogen-Vacancy Center in Nanodiamonds to a Single Organic Molecule", ACS Nano, vol. 5, No. 10, Sep. 7, 2011, pp. 7893-7898.
Yamanaka et al., "SAX Microscopy with Fluorescent Nanodiamond Probes for High-Resolution Fluorescence Imaging", Biomedical Optics Express, 2(7):1946-1953 (2011).
Zou et al. "Fabrication of Diamond Nanopillars and Their Arrays", Applied Physics, letters 92, 053105 (2008).

\* cited by examiner

CONJUGATES OF NANO-DIAMOND AND MAGNETIC OR METALLIC PARTICLES

CROSS-REFERENCE TO RELATED APPLICATIONS

This application is a continuation of U.S. patent application Ser. No. 14/150,412, filed Jan. 8, 2014, which is a continuation of International Patent Application No. PCT/US2012/048830, filed Jul. 30, 2012, which is related to U.S. Provisional Application Ser. No. 61/513,830, filed Aug. 1, 2011, 61/549,046, filed Oct. 19, 2011, 61/562,551, filed Nov. 22, 2011, 61/591,570, filed Jan. 27, 2012, and 61/624,647, filed Apr. 16, 2012, each of which are hereby incorporated herein by reference in their entirety and from which priority is claimed.

STATEMENT OF FEDERALLY SPONSORED RESEARCH OR DEVELOPMENT

This invention was made with government support under grant Nos. AFOSR PECASE FA9550-12-1-0045 and FA9550-11-1-0014, awarded by the Air Force Office of Scientific Research. The government has certain rights in the invention.

BACKGROUND

The disclosed subject matter relates generally to techniques for fabricating conjugates of nano-diamond and magnetic or metallic particles for use in imaging and sensing applications.

Fluorescent biomarkers are used in a wide range of applications in biology, chemistry, and other fields. Certain biomarkers can have brightness approximately around an order of magnitude of less than 10^5 counts/sec, can bleach, blink, or degrade during excitation, and/or are toxic to cells. Optical probes that are non-toxic and efficient and stable light emitters are desirable to sensing in biology and medicine.

Additionally, resolution for imaging with conventional fluorescent biomarkers can be limited by the optical diffraction limit of $$\frac{\lambda}{2NA} \sim 250 \text{ nm.}$$

Accordingly, techniques providing resolution below the diffraction limit are also desirable.

SUMMARY

In one aspect of the disclosed subject matter, a method for imaging a characteristic of sample includes providing a plurality of conjugates of diamond-magnetic nanoparticles, one or more of which including a nitrogen vacancy center. The conjugates can be exposed to the sample. The nitrogen vacancy centers can be pumped with a pump light and one or more microwave pulses can be applied. The fluorescent response of the nitrogen vacancy center can then be detected.

In one embodiment, the diamond-magnetic conjugates can include a diamond nanoparticle coupled to a magnetic nanoparticle at a predetermined distance corresponding to a radiative enhancement. Additionally or alternatively, the individual diamond-magnetic conjugates can have a variety of alignments between the magnetic field of the magnetic nanoparticle and the axis of a nitrogen vacancy center in the diamond nanoparticle.

In one embodiment, optically pumping can include directing a continuous wave of pump light. Alternatively, optically pumping can include applying a pulse of pump light prior to applying the at least one microwave pulse and applying an additional pulse of pump light subsequent to applying the at least one microwave pulse.

In one embodiment, detecting a fluorescent response can include detecting emitted photons over an area of the sample. The area of the sample can be divided into a set of pixels. For each pixel, a first, second, and third microwave pulse can be applied and the intensity of a corresponding fluorescent response can be measured. The first frequency can be tuned to a field splitting frequency of the nitrogen vacancy center of one of the conjugates and can correspond to the $m_s=+1$ spin sublevel. The second frequency can be tuned to the zero filed splitting frequency of the nitrogen vacancy center of the nitrogen vacancy center. The third frequency can be tuned to a field splitting frequency of the nitrogen vacancy center of the nitrogen vacancy center. The location of the nitrogen vacancy center can be determined based on the first, second, and third intensities.

In one embodiment, the characteristic of the sample can be magnetic field. For example, a local magnetic field at the location of the nitrogen vacancy center can be determined based on a first, second, and third intensity measurement corresponding to a first, second, and third microwave pulse. Additionally or alternatively, the characteristic of the sample can be pH concentration. For example, the pH concentration can be inferred from, based on the fluorescence response, a determined rate of ionization or reduction of the nitrogen vacancy center. Additionally or alternatively, the characteristic of the sample can be electric field. For example, the electric field can be inferred from, based on the fluorescent response, a determined rate of switching between different charge states of the nitrogen vacancy center. In certain embodiments, the diamond-magnetic conjugates can be bound to a biological molecule.

In another aspect of the disclosed subject matter, a method for fabricating diamond-metal conjugates can include depositing a monolayer of diamond nanoparticles having a predetermined radius on a substrate. The surface of the substrate can be etched to a depth greater than the predetermined radius of the diamond nanoparticles. A layer of metal having a predetermined thickness can be deposited over the monolayer of diamond nanoparticles. The predetermined thickness can correspond to a radiative enhancement rate of a nitrogen vacancy center in a diamond nanoparticle. The metal-covered diamond nanoparticles can be transferred to a second substrate.

In certain embodiments, the metal layer can include gold, silver, or a combination thereof. Additionally or alternatively, the metal layer can include a metallic metal, for example nickel, cobalt, iron, and/or chemical compounds thereof. In one embodiment, the layer of metal can be deposited at an angle.

In another aspect of the disclosed subject matter, a method for fabricating diamond-metal conjugates can include preparing a surface of diamond nanoparticles with an acid treatment. The diamond nanoparticles can undergo silanization with amino-teminated silanes to provide an amine on the surface of the diamond nanoparticles. A surface of the metal nanoparticles can be prepared with a molecule, the molecule having an affinity to bond with the amine. The diamond nanoparticles and metal nanoparticles can be mixed in a solution, whereby the molecule of the surface of the metal nanoparticles can bond to the amine of the surface of the diamond nanoparticles, thereby forming a diamond-metal conjugate.

In one embodiment, the amine is an amine with a length corresponding to a radiative enhancement rate of a nitrogen vacancy center in a diamond nanoparticle. In certain embodiments, the metal nanoparticles can include gold, silver, or a combination thereof. Additionally or alternatively, the metal nanoparticles can include a metallic metal, for example nickel, cobalt, iron, and/or chemical compounds thereof.

In another aspect of the disclosed subject matter, a method for fabricating diamond-metal conjugates can include preparing a surface of diamond nanoparticles with an acid treatment. The surface of at least one of the diamond nanoparticles can be adapted to link to a first end of a DNA strand. Metal nanoparticles adapted to link to a second end of the DNA strand can be provided. The diamond nanoparticles and the metal nanoparticles can be mixed in solution with the DNA strand.

In one embodiment, the DNA strand can have a length corresponding to a radiative enhancement rate of the nitrogen vacancy center of a diamond nanoparticle. In certain embodiments, the metal nanoparticles can include gold, silver, or a combination thereof. Additionally or alternatively, the metal nanoparticles can include a metallic metal, for example nickel, cobalt, iron, and/or chemical compounds thereof.

Throughout the drawings, the same reference numerals and characters, unless otherwise stated, are used to denote like features, elements, components or portions of the illustrated embodiments. Moreover, while the disclosed subject matter will now be described in detail with reference to the Figs., it is done so in connection with the illustrative embodiments.

DETAILED DESCRIPTION

Techniques for fabricating conjugates of nano-diamond and magnetic or metallic particles for use in imaging and sensing applications are disclosed herein.

The nitrogen-vacancy (NV) center in diamond can serve as a biomarker. Diamond NV color centers can be formed when a substitutional nitrogen lodges itself in the carbon lattice, replacing two carbons and creating a physical vacancy with dangling bonds. Diamond NV centers can occur naturally or can be implanted in a diamond structure via ion radiation or the like. The NV− center has an additional electron associated with it, creating a desirable electronic $S=1$ structure that has a long-lived spin triplet in its ground state that can be probed using optical and microwave excitation. The NV electron spin can act as a sensitive probe of the local environment, and their optical accessibility can allow their use in optically-detected magnetic resonance schemes.

Figure 1:
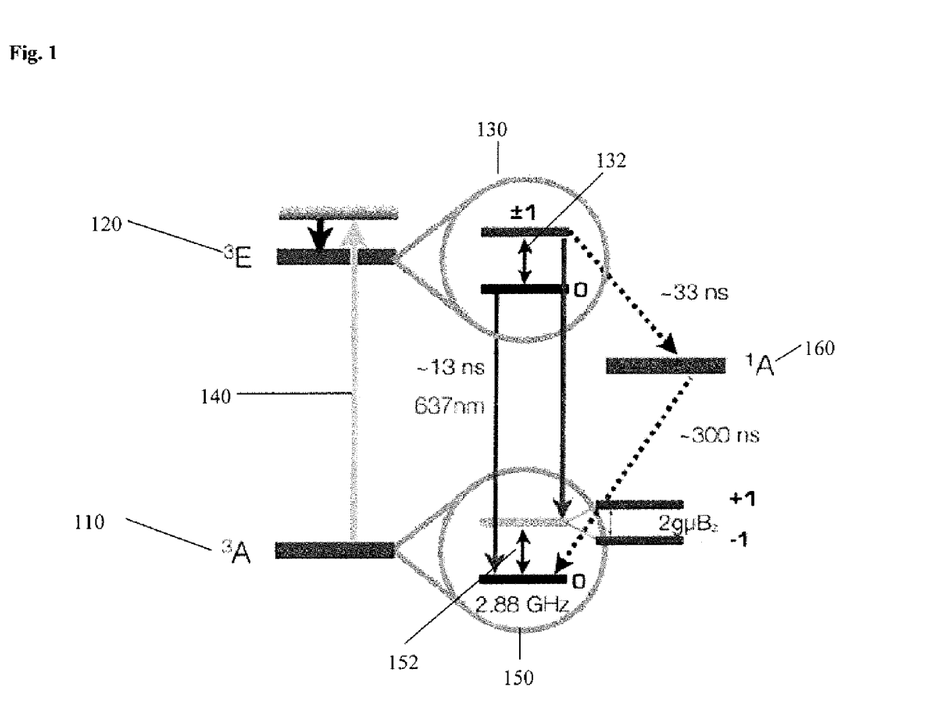
FIG. 1 is a diagram showing a nitrogen-vacancy (NV) center in diamond.

Referring to FIG. 1 an exemplary NV center is illustrated. NV centers can absorb photons 140 with a wavelength around 532 nm and emit a fluorescent (PL) response, which can be between 637 and 800 nm. A spin-dependent intersystem crossing 160 between excited state 120 triplet (3) to a metastable, dark singlet level 110 (S) can change the integrated PL for the spin states $|0\rangle$ and $|\pm1\rangle$. The deshelving from the singlet 110 occurs primarily to the $|0\rangle$ spin state, which can provide a means to polarize the NVC.

As depicted in FIG. 1, transitions from the NV ground state 110 to the excited state 120 are spin-conserving, keeping $m_s$ constant. Such an excitation can be performed using laser light at approximately 532 nm 140; however, other wavelengths can be used, such as blue (480 nm) and yellow (580 nm). While the electronic excitation pathway preserves spin, the relaxation pathways contain non-conserving transitions involving an intersystem crossing (or singlet levels).

In accordance with the disclosed subject matter, the NV centers can be used, for example, for voltage imaging. Spin states in the diamond can enable electric and magnetic field sensing on the nanometer scale with high precision at room temperature. Furthermore, the NV centers can be uniquely identified by transitions between their magnetic sublevels, a property that can enable sub-optical spatial resolution. For example, single NVs can be deterministically switched to locate emitters below 30 nm resolution. Diamond nanoprobes with the NV can also be photostable. For example, single NV centers can emit without a change in brightness for months or longer. Additionally diamond is chemically inert, cell-compatible, and has surfaces that can be suitable for functionalization with ligands that target biological samples. NV centers can emit in excess of $10^6$ photons per second, far brighter than certain other light emitters.

In accordance with one aspect of the disclosed subject matter, a diamond nanoparticle including at least one NV center can be coupled to a metal nanostructure to increase the brightness of the emitter. Conjugates of diamond nanoparticles and metallic nanostructures can act as a stable emitter-antenna system. For example, the NV center can be coupled with a larger optical dipole, which can amplify the dipole of the NV center, acting as a nano-antenna.

Figure 2:
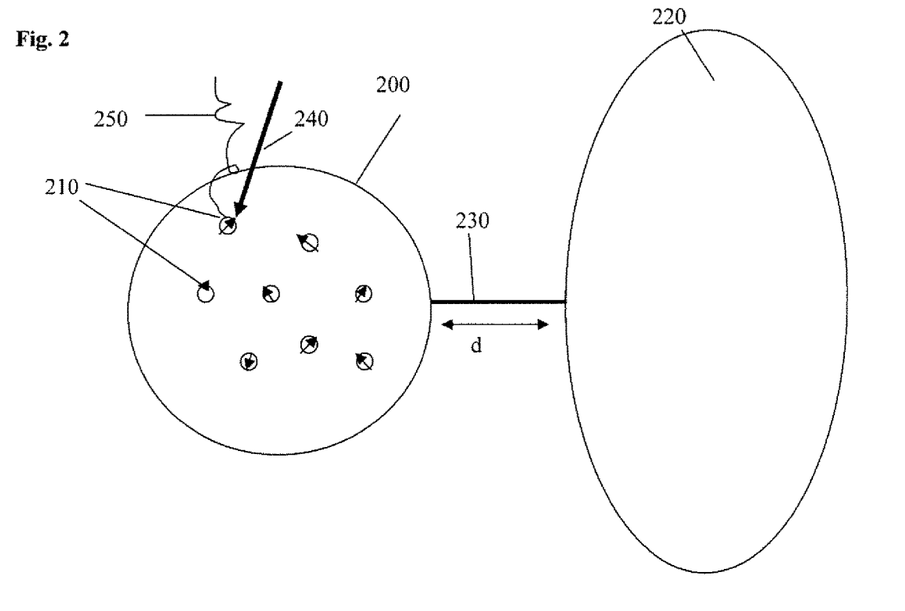
FIG. 2 is a block diagram of a conjugate of a diamond nanoparticle and a metallic nanoparticle in accordance with an embodiment of the disclosed subject matter.

With reference to FIG. 2 a conjugate of diamond nanoparticles and metallic nanostructures in accordance with an embodiment of the disclosed subject matter will be described. A diamond nanoparticle 200 can contain at least one nitrogen vacancy center 210. The diamond nanoparticle 200 can be coupled to a magnetic nanostructure 220, for example as described below. The diamond nanoparticle 200 can be attached to the magnetic nanostructure 220 at a distance d 230. For example, in an embodiment of the disclosed subject matter, the distance d 230 can correspond to an radiative enhancement of the at least one NV center 210. In some embodiments, the distance d 230 can be predetermined such that the optical dipole of the magnetic nanostructure 220 is located a predetermined distance from the at least one NV center 210.

The conjugate of diamond nanoparticles and metallic nanostructures can be pumped with pump light 240. The pump light 240 can have a wavelength suitable to optically excite the NV center 210. For example, the pump light 240 can have a wavelength of approximately 532 nm. When a photon from the pump light 240 is absorbed by the NV center 210, an electron associated with the NV center 210 can transition to an excited state 120, and then transition back to the ground state 110 and emit a photon 250. The emitted photon 250 can have a wavelength of between 637 nm and 800 nm.

A microwave pulse can be tuned to the field splitting frequency of the nitrogen vacancy center 210 can drive the NV state from the $m_s=0$ state to the $m_s=\pm 1$ state. The can be prepared in the ground state through optical pumping at 532 nm, as a distribution of NV's in various $m_s$ sublevels will eventually tend to $m_s=0$. When observing emitted photons, for example with a photon detector, the fluorescence from the zero phonon line (ZPL) and phonon sideband (PSB), relaxation through the singlet levels can reduce observed counts. Thus, applying microwaves tuned to a frequency approximately equal to the zero-filed splitting, D, can cause a drop in the fluorescence from the ZPL. Additionally or alternatively, NV spin state information can be gathered by observing the singlet level transition at 1042 nm. The application of a small magnetic field Bz on the NV-symmetry axis breaks the degeneracy in the ±1 sublevels due to the well-known Zeeman effect.

The diamond nanoparticle 200 can have a diameter between approximately 2 nm and hundreds of nanometers. In an exemplary embodiment, the diamond nanoparticle 200 can have a diameter, for example, between approximately 20 nm and approximately 40 nm. The metallic nanostructrure 220 can have a diameter, for example, between approximately 5 nm and hundreds of nanometers. In an exemplary embodiment, the metallic nanostructure 220 can have a diameter, for example, between approximately 5 nm and approximately 35 nm. In an exemplary embodiment, for example, a gold nanostructure can have a diameter approximately equal to 30 nm, whereby the plasmon resonance corresponds to a radiative enhancement of the diamond NV fluorescence from 640-720 nm. The metallic nanostructure 220 as disclosed herein can be, for example, a non-magnetic particle such as gold or silver. Alternatively, the metallic nanostructure 220 can be a super-paramagnetic particle or other magnetic nanoparticles. For example, the metallic nanostructure 220 can include nickel, cobalt, iron, or chemical compounds thereof, including oxides such as iron oxide.

Figure 3:
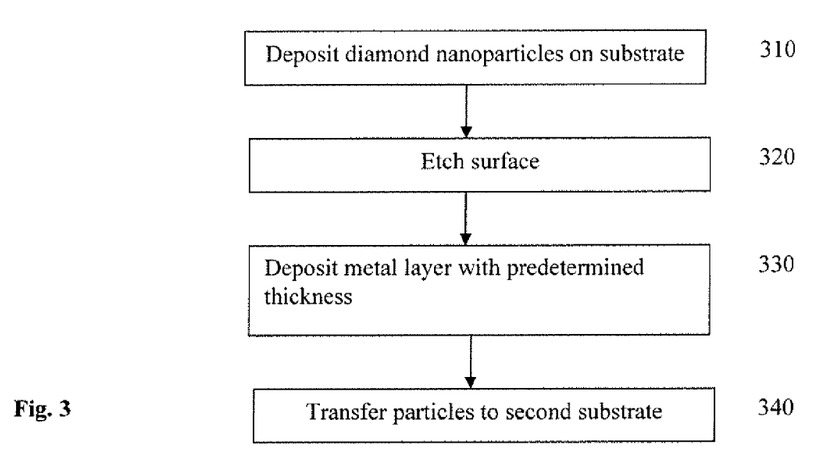
FIG. 3 is a flow diagram illustrating a process of fabricating a diamond-metal conjugate in accordance with one embodiment of the disclosed subject matter.

With reference to FIG. 3, an illustrative method for fabricating hybrid diamond-metal or diamond-magnetic particle single photon emitters can include attaching a metal nanoparticle to a diamond nanoparticle. In one embodiment, a method for fabricating hybrid diamond-metal single photon emitters can include physical deposition of a metal onto the diamond nanoparticles. The metal can be, for example, gold, silver, or a combination thereof. Alternatively, the metal can have magnetic properties and can include, for example, nickel, cobalt, iron, or chemical compounds thereof, including oxides such as iron oxide. A monolayer of diamond nanoparticles, at least some of which having at least one nitrogen vacancy center, having a predetermined radius can first be deposited (310) on a substrate. The surface of the substrate containing the diamond nanoparticles can be etched (320) to a depth greater than the depth of the predetermined radius. A layer of metal can then be deposited (330) up to a predetermined thickness over the monolayer of diamond nanoparticles. The thickness of the layer of metal can correspond to a radiative enhancement rate based on the predetermined radius of the diamond nanoparticles. For example, as noted previously, a 30 nm thick gold layer can produce strong radiative enhancement as the plasmon frequency matches the emission of the $NV^-$ center. The diamond-metal conjugates can then be transferred (340) from the first substrate to a second substrate.

The diamond nanoparticles can range from approximately 2 to hundreds of nanometers. Diamond nanocrystals can be produced by high-temperature, high-pressure growth; by detonation; and by fracturing/milling of larger diamonds. They can be purchased commercially and then cleaned using strong acids, as those skilled in the art will appreciate.

Etching (320) can include, for example, reactive ion etching. Reactive ion etching can include the use of, for example, an oxygen or chlorine plasma. For example, reactive ion etching (RIE) can be used with a 10:1 gas mixture of Cl2 and O2 in a Oxford Plasmalab 100 ICP etcher. Using 3 mTorr pressure and DC bias power of 1000 W, with the diamond plate at 60 C during the etching process, etching at 17 nm/second can be realized.

The layer of metal can be deposited (330) by sputter deposition, which is a form of physical vapor deposition in which a metal target can ejected and then deposited onto the target sample. For example, A Kurt J. Lesker Co. PVD75 electron beam evaporator can be operated at $10^{-5}$ torr to evaporate about at a rate of about 0.3-1 nm/sec.

In some embodiments, the layer of metal can be deposited at an angle using a sample holder that is angled with respect to the sputter beam direction.

The thickness of the layer of metal can correspond to a radiative enhancement rate based on the radius of the diamond nanoparticles. The thickness of the metal can be chosen so that the surface plasmon polariton resonance frequency matches the emission spectrum of the NV, e.g., from 630-720 nm. For example, spherical gold particles are can be about 30 nm in diameter for suitable radiative enhancement.

The diamond-metal conjugates can be transferred (340) from the first substrate to the second substrate by pressing an adhesive surface against the surface of the diamond-metal conjugates. For example, the second substrate can be a material with adhesive properties, such as PDMS/silicone. Alternative, a sharp knife edge or abrasive surface can be used to cut off or grind off the nanoparticles.

Figure 4:
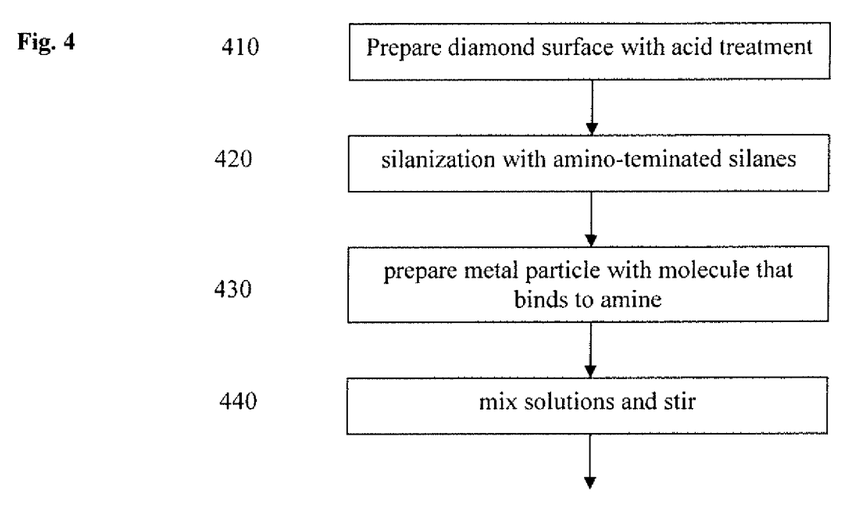
FIG. 4 is a flow diagram illustrating a process of fabricating a diamond-metal conjugate in accordance with another embodiment of the disclosed subject matter.

In another embodiment of the disclosed subject matter, and with reference to FIG. 4, a method of fabricating hybrid diamond-metal single photon emitters can include mixing diamond nanoparticles and metal nanoparticles in a solution. The diamond and metal nanoparticles can be functionalized to bind together at a predetermined distance. This predetermine distance can correspond to a desired radiative enhancement.

The conjugation can be achieved by first preparing (410) the diamond surface through a strong acid treatment, followed by silanization (420) with amino-teminated silanes. The metal particles can be prepared (430) with a molecule that binds to the amine. The two solutions can be mixed together and stirred (440). The length of the amine that is used in this reaction to bind the metal and diamond particles can determine the separation between the two.

Figure 5:
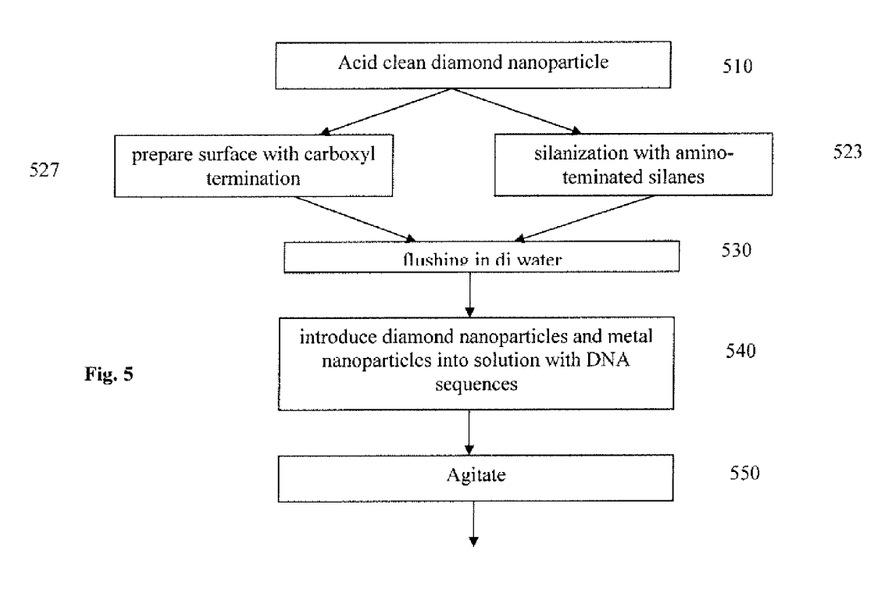
FIG. 5 is a flow diagram illustrating a process of fabricating a diamond-metal conjugate in accordance with another embodiment of the disclosed subject matter.

In another embodiment, and with reference to FIG. 5, an example method of fabricating hybrid diamond-metal single photon emitters can include attaching a single strand of DNA to a diamond nanoparticle and attaching a second single strand of DNA to a metal or magnetic particle. Diamond nanocrystals can be cleaned with acid (510) to prepare their surface state with carboxyl termination (527). Alternatively, the nanodiamonds can be acid cleaned followed by silanization with amino-teminated silanes (523). The acid can removed by repeated flushing (530) in Dl water. Gold or other particles can be purchased with similar surface preparations from companies such as Sigma Aldrich. The DNA sequences can have "sticky" ends, such as $NH_2$, and can be used to link the surface-treated diamond and metal particles. Suitable DNA strands can be obtained commercially. The metal particles and diamond nanoparticles can be mixed (540) in equal number in a solution with DNA binding strands and agitated (550). The solution can be agitated (550), for example by sonication.

The techniques disclosed herein can provide for bright, photostable atomic defect centers that emit at unique wavelengths ranging from the ultraviolet to the infrared. Emitters coupled to metal particles, as disclosed herein, can emit faster through an enhanced effective electromagnetic dipole, via the metal's surface plasmon polarization mode.

In another aspect of the disclosed subject matter, a method for imaging and tracking individually addressable emitters can include using the conjugates of diamond nanoparticle and magnetic nanoparticles disclosed above.

Figure 6:
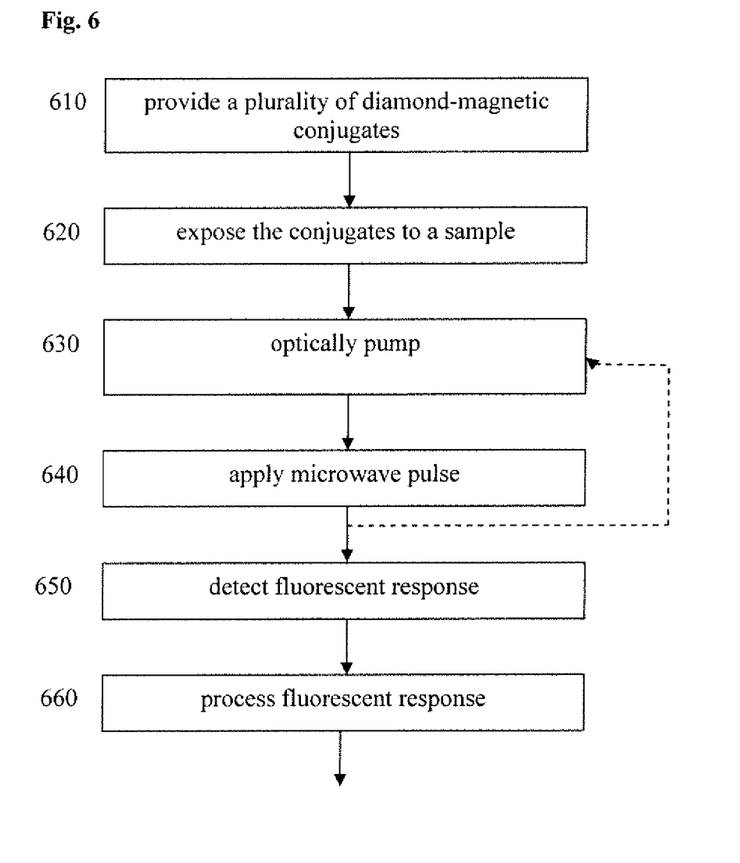
FIG. 6 is a flow diagram illustrating a method for imaging a characteristic of a sample in accordance with an embodiment of the disclosed subject matter.

In one embodiment, the diamond NV can sense the magnetic field of the magnetic particle, which can enable the NV sensor to detect the location and orientation of the magnetic particle. Conjugates of diamond nanoparticles with NV centers coupled to magnetic nanoparticles having a diameter between approximately 5 nm and approximately 35 nm can be provided (610) and exposed (620) to a sample for massively parallel multi-spectral imaging and tracking within liquid environments. For example, the magnetic nano-particle can impart on the NV− electronic ground states a Zeeman splitting. The value of the Zeeman splitting can depend on the precise alignment between the NV− and magnetic nano-particle, and this alignment can be random, allowing for thousands of different values. The splitting can remain the same even as the conjugates tumble in a liquid. Thus, a large number of different Zeeman splittings—on the order of thousands—are available for different diamond-magnet conjugates. These conjugates therefore can correspond to a large number of different colors (in the microwave regime), which can be used to track distinguishable particles under a microscope, with a sub-wavelength resolution. Furthermore, different groups of conjugates can be prepared and functionalized with different compounds, enabling labeling with several thousands of different conjugates that can be optically located to sub-10 nm.

In one embodiment, techniques for imaging a plurality of diamond-magnetic nanoparticle conjugates can include observation (650) of optically detected electron spin resonance (ESR) using microwave transitions (640) within the NV's magnetic sublevels. The NV has a spin-triplet ground state with sublevels corresponding to the spin projections of $m_s=0,1,−1$. The microwave transitions between these levels are on the order of 2.87 GHz in the absence of a magnetic field. When a field is present, such as produced by the magnetic nanoparticle coupled to the diamond, the $m_s=−1,+1$ sublevels can experience an energy shift via the Zeeman effect, which can be proportional to the dot product between the magnetic field and the NV spin axis. This energy shift can be observed (650) by optically detected ESR; from its magnitude, the magnetic field strength can be inferred (660). Moreover, because the magnetic particle's dipole orientation and the NV's orientation are random, a continuous distribution of different Zeeman splittings can be obtained using a plurality of diamond-magnetic nanoparticle conjugates.

Figure 7:
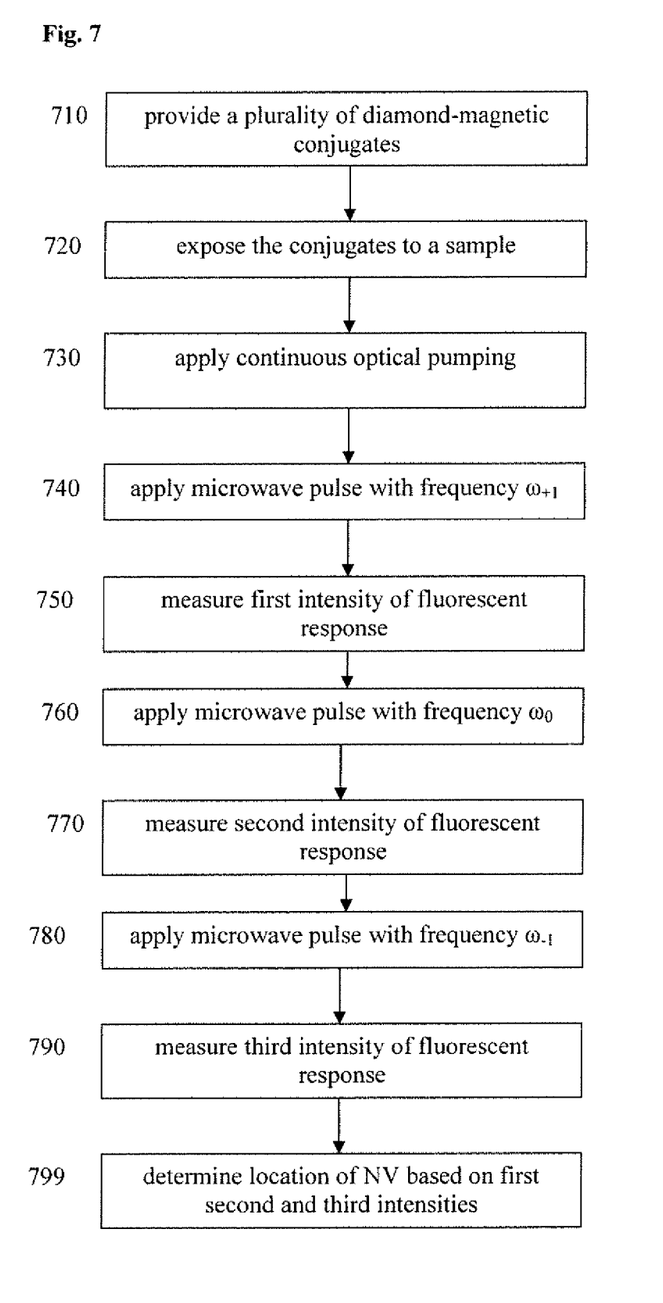
FIG. 7 is a flow diagram illustrating a method for imaging a characteristic of a sample in accordance with another embodiment of the disclosed subject matter.
Figure 8:
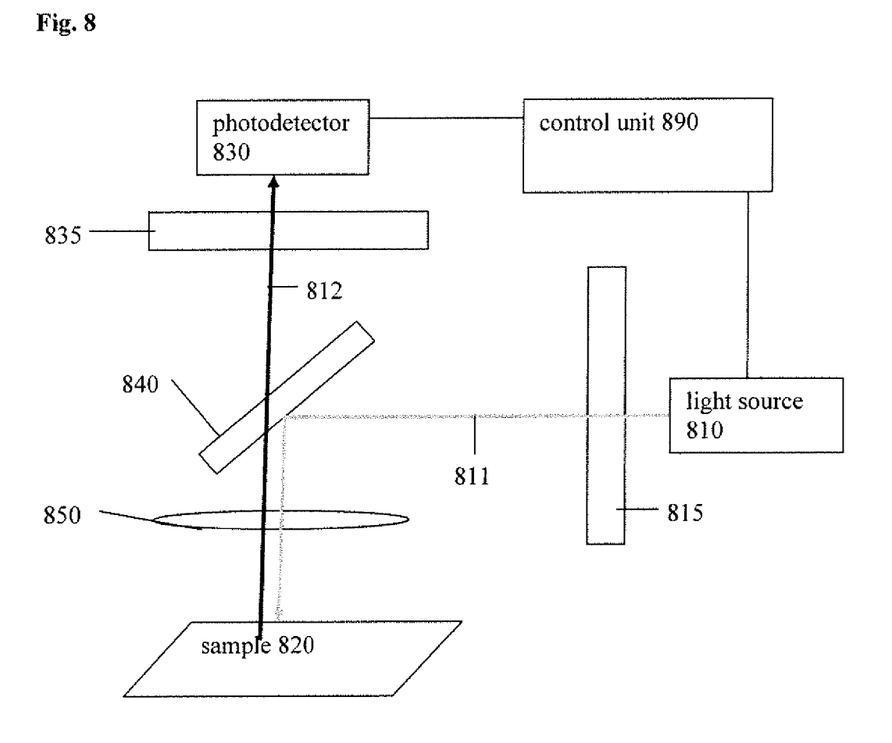
FIG. 8 is a schematic diagram of a system for imaging a characteristic of a sample in accordance with another embodiment of the disclosed subject matter.

An exemplary embodiment in which individual NVs can be uniquely addressed will now be described with reference to FIG. 7 and FIG. 8. However, various modifications will become apparent to those skilled in the art from the following description and the accompanying figures. Such modifications are intended to fall within the scope of the appended claims.

In this embodiment, a confocal scanning technique or emCCD camera technique can be employed. Any suitable emCCD can be employed, for example the ProEM available from Princeton Instruments. In general, a two-dimensional scan of a sample with m NV centers can be given by:

$$I(x,y,\omega)=\Sigma_i^m I_i \alpha_i [1-D_i(P_{RF},P_{pump},\omega)N_i(x,y)], \quad (1)$$

where I is intensity, $\alpha$ is collection efficiency; $D_i$ is electron spin resonance dips; $P_{RF}$ is power of the radio-frequency field; $P_{pump}$ is the power of the optical 532 nm pump field; $\omega$ is the crystal field splitting frequency, and N is a two-dimensional Gaussian distribution with general defining parameters. A confocal scan taken off resonance can be subtracted from a confocal scan taken on resonance to isolate only the photons emitted from the NVs with frequencies $\omega_i$, given by:

$$I(x,y,\omega_O)-I(x,y,\omega_i)=I_i \alpha_i C_i (P_{RF},P_{pump})N_i(x,y) \quad (2)$$

$D_i$ can be given by:

$$Di(P_{RF}, P_{pump}, \omega) = \frac{C_i(\gamma_i/2)^2}{(\gamma_i/2)^2 + (\omega - \omega_i)^2}, \quad (3)$$

where $C_i(P_{RF}, P_{pump})$, $\gamma_i(P_{RF}, P_{pump})$, and $\omega_i=\omega_O \pm \vec{B} \cdot \vec{\mu}_i$. $N_i(x,y)$ can be given by:

$$N_i(x, y) = \frac{e^{-\frac{1}{2(1-\rho_i^2)} \left[ \frac{(x-\mu_{ix})^2}{\sigma_{ix}^2} + \frac{(x-\mu_{iy})^2}{\sigma_{iy}^2} - \frac{2\rho_i(x-\mu_{ix})(x-\mu_{iy})}{\sigma_{ix}\sigma_{iy}} \right]}}{2\pi\sigma_{ix}\sigma_{iy}\sqrt{1-\rho_i^2}}. \quad (4)$$

The precision with which the two-dimensional position of the NV center can be known can increase with the square root of the integration time due to the poissonian nature of the source. Such precision can be limited by the environment, including piezoelectric drift of a sample holder and thermal fluctuations throughout the setup.

The Zeeman splitting of an NV center can be measured by using optically detected magnetic resonance (ODMR). For example, a continuous wave of green pump laser can be applied for polarizing the spin of the NV into the $m_s=0$ ground state, and a microwave field in the GHz regime can resonantly excite the NV from the $m_s=0$ ground state to the $m_s=\pm 1$ ground states. Due to the bias of the $m_s=\pm 1$ excited states to decay into a metastable singled state with a longer life (e.g., 300 ns) than the lifetime of the $m_s=0$ excited state (e.g., 10 ns), the fluorescence into the 637-800 nm band can decrease.

A plurality of conjugates of diamond magnetic nanoparticles can be provided (710). One or more of the conjugates can have a nitrogen vacancy center within its diamond nanoparticle. The plurality of conjugates can be exposed (720) to a sample 820. The sample 820 can be a fluid, such as a biological fluid or a substrate in the solid state, such as a circuit. In some embodiments, the conjugates can be exposed to a sample within a tissue. For example, the conjugates can be introduce into a cell or into a lumen.

The conjugates can be optically pumped (730) to excite the nitrogen vacancy centers contained therein. For example, the conjugates can be continuously pumped with green laser at approximately 532 nm with a power near 1 mW focused to a 500 nm spot. For pulsed excitation, the power can scale down with the duty cycle. In some embodiments, optical pumping can occur at discrete times. For example, a first pulse of pump light can be applied to drive the NV spin states into the $m_s=0$ sublevel. An additional pulse of pump light can be applied for readout.

Optical pumping (730) can be accomplished with a suitable light source 810, which can include a green laser capable of emitting light at 532 nm. Addition optics 815 and 835 can be employed to guide, filter, focus, reflect, refract, or otherwise manipulate the light. Such optics can include, for example, a pinhole aperture and/or barrier filter (not shown). Additionally, a dichromatic mirror 840 can be used to direct pump light to the sample 820 while transmitting a PL response. For example, the light source 810 can be arranged such that pump light 811 is reflected off of a dichromatic mirror 840 and towards the sample 820. A PL response from the sample will be directed through the dichromatic mirror 840 in a direction orthogonal to the orientation of the light source 810.

The pump light 811 can be directed through an objective 850 to the sample 820. Photons in the pump light 811 can be absorbed by the NV centers within the conjugates exposed to the sample 820, thereby exciting the NV center into an excited state. The NV can then transition back to the ground state, emitting fluorescent response 812, e.g., a photon with a wavelength between 637 and 800 nm. This fluorescent response can pass through the objective 850 and the dichromatic mirror 840 to a photodetector 830. In certain embodiments, the photodetector 830 can include a photomultiplier. The photodetector 830 can be, for example, an emCCD camera. Alternatively, the photodetector 830 can be a scanning confocal microscope or other suitable photon detector.

In certain embodiments, the axis of the nitrogen vacancy centers in the diamond nanoparticle of the conjugate can be aligned random angles with the magnetic field of the magnetic nanoparticle. The magnetic nano-particle can impart on the NV− electronic ground states a Zeeman splitting between the $m_s=+1$ and a $m_s=+1$ spin sublevels. The value of the Zeeman splitting can depend on the precise alignment between the NV− and magnetic nano-particle, and this alignment can be random, allowing for thousands of different values.

The area of the sample 820 can be divided into a number of pixels, each pixel corresponding to subset of the area. For each pixel, the fluorescent response 812 can be measured for various microwave pulses. In this manner, the location of a single NV center can be addressed due to the particular Zeeman splitting resulting from the precise alignment between the magnetic nanoparticle and the NV center. For example, a first microwave pulse can be applied (740) at a first frequency $\omega_{+1}$. This first frequency can be tuned to the field splitting frequency of a single NV center based on its Zeeman splitting. This microwave pulse can drive the single NV center into the $m_s=+1$ state, which can result in lower resulting fluorescent intensity due to transition through the shelving state. However, this pulse will not drive any surrounding NV centers into the $m_s=+1$ state because different orientations of the their corresponding magnetic nanoparticles will result in different Zeeman splitting. The photodetector 830 can then measure (750) the intensity of the fluorescent response.

A second microwave pulse can be applied (760) at a second frequency $\omega_0$. The second frequency can be tuned to the zero field splitting frequency of a single NV center, e.g., 2.87 GHz. The photodetector 830 can then measure (770) the intensity of the fluorescent response. In like fashion, at least a third microwave pulse can be applied (780) at a third frequency $\omega_{+1}$. The third frequency can be tuned to the field splitting frequency of a single NV center based on its Zeeman splitting. This microwave pulse can drive the single NV center into the $m_s=-1$ state, which can result in lower resulting fluorescent intensity due to transition through the shelving state. The photodetector 830 can then measure (790) the intensity of the fluorescent response.

The location of the single NV center can then be determined (799) based on the intensities of the fluorescent responses corresponding to the first, second, and third microwave pulses. For example, the control unit 890, which can include a processor and a memory, can subtract the intensities corresponding to frequencies $\omega_{+1}$ and $\omega_{-1}$ from the intensity corresponding to co. Additional processing techniques can be employed to further reduce uncertainty regarding the position of the NV center.

Each pixel can then be combined and displayed, thereby providing a graphical representation or image of the location of one or more NV centers. The techniques disclosed herein can be repeated for a plurality of NV centers, which can allow for tracking of individual NV centers.

In one embodiment, the diamond-magnet nanoparticle conjugates can be coupled with a protein for biological imaging. The binding can employs surface functionalization of the nanodiamond, for example via carboxyl groups or silanization with ammene groups. Carboxyl or ammene groups can be, for example, paired with DNA or antibodies for selective binding to a particular kind of protein to be studied. Once the diamond-magnet is linked to the protein, optical electron spin techniques, as disclosed herein, can be used to measure properties of the protein, such as its chemical composition or oxidative state. The chemical composition can be inferred by magnetic resonance imaging of its constituent atoms. The oxidative state can be inferred from spin noise due to a free electron, or oxidation-state-dependent paramagnetic/diamagnetic state of certain molecules such as hemoglobin. The magnetic nanoparticle in the diamond-magnet conjugates can produce a sharp magnetic field gradient that causes different Zeeman splittings of protein molecules as a function of their position within the magnetic field. Additionally, the Zeeman splitting between the magnetic particle and NV can be used to uniquely identify a particular NV-nanodiamond-protein conjugate through the electron spin signal, which can allow for the tracking of a single conjugate within a cell or other fluid environment, or to address it using super-resolution imaging, for example as disclosed above.

In one embodiment, the diamond-magnet nanoparticle conjugates can be used for high resolution imaging of a magnetic field. The magnetic particle-NV conjugate can have a unique ground state Zeeman splitting that can enable super-resolution imaging using deterministic emitter switch microscopy, as disclosed herein. In addition, the response of the magnetic nanoparticle can be used to more precisely measure the local magnetic field environment, as it can act as an amplifier of the magnetic field. The magnetic field can then be determined using the Zeeman splitting of the NV magnetic sublevels.

In one embodiment, the diamond-magnet nanoparticle conjugates can be used for high resolution imaging of electric field and pH. pH concentration can be measured by the rate of reduction/ionization of an NV that is located approximately 2-30 nm below the diamond surface. The reduction and ionization can produces different NV charge states, including $NV^{2+}$, $NV^+$ $NV^0$, and $NV^-$. These different charge states can be associated with different emission spectra. By measuring the rate of switching between different charge states and the mean occupation of these charge states, one can infer information about the local charge electric field and the local charge environment and abundance of radicals.

The presently disclosed subject matter is not to be limited in scope by the specific embodiments herein. Indeed, various modifications of the disclosed subject matter in addition to those described herein will become apparent to those skilled in the art from the foregoing description and the accompanying figures. Such modifications are intended to fall within the scope of the appended claims.

The invention claimed is:

1. A nanoparticle diamond-metal conjugate, comprising:
a diamond nanoparticle having a nitrogen vacancy center;
a metallic nanostructure,
wherein the diamond nanoparticle has a predetermined radius and is at least partially directly attached to a layer of the metallic nanostructure and wherein the nitrogen vacancy center is located at a distance d based at least in part on the predetermined radius of the diamond nanoparticle.

2. The nanoparticle diamond-metal conjugate of claim 1, wherein the metallic nanostructure comprises a magnetic nanoparticle.

3. The nanoparticle diamond-metal conjugate of claim 2, wherein the distance d is a predetermined distance corresponding to a radiative enhancement of the nitrogen vacancy center.

4. The nanoparticle diamond-metal conjugate of claim 2, wherein the distance d corresponds to an optical dipole of the magnetic nanoparticle being a predetermined distance from the nitrogen vacancy center.

5. The nanoparticle diamond-metal conjugate of claim 1, wherein the metallic nanostructure comprises the layer of metal having a predetermined thickness deposited over the diamond nanoparticle, the predetermined thickness corresponding to a radiative enhancement rate of the nitrogen vacancy center.

6. The nanoparticle diamond-metal conjugate of claim 5, wherein the layer of metal comprises a metal selected from the group consisting of gold, silver, or a combination thereof.

7. The nanoparticle diamond-metal conjugate of claim 5, wherein the layer of metal comprises a magnetic layer.

8. The nanoparticle diamond-metal conjugate of claim 7, wherein the layer of metal comprises a metal selected from the group consisting of nickel, cobalt, iron, or chemical compounds thereof.

9. The nanoparticle diamond-metal conjugate of claim 1, wherein a surface of the diamond nanoparticle is prepared with an acid treatment and treated with one or more amino-teminated silanes to provide an amine on the surface of the diamond nanoparticle,
a surface of the metal nanostructure is prepared with a molecule having an affinity to bond with the amine, and
the molecule of the surface of the metal nanostructure bonds to the amine of the surface of the diamond nanoparticle.

10. The nanoparticle diamond-metal conjugate of claim 9, wherein the amine has a length corresponding to a radiative enhancement rate of the nitrogen vacancy center.

11. The nanoparticle diamond-metal conjugate of claim 9, wherein the metal nanostructure comprises a metal selected from the group consisting of gold, silver, or a combination thereof.

12. The nanoparticle diamond-metal conjugate of claim 9, wherein the metal nanostructure comprises a magnetic layer.

13. The nanoparticle diamond-metal conjugate of claim 12, wherein the metal nanostructure comprises a metal selected from the group consisting of nickel, cobalt, iron, or chemical compounds thereof.

14. The nanoparticle diamond-metal conjugate of claim 1, wherein a surface of the diamond nanoparticle is prepared with an acid treatment and adapted to link to a first end of the DNA strand,
the metal nanostructure is adapted to link to a second end of the DNA strand.

15. The nanoparticle diamond-metal conjugate of claim 14, wherein the DNA strand comprises a DNA strand having a length corresponding to a radiative enhancement rate of the nitrogen vacancy center.

16. The nanoparticle diamond-metal conjugate of claim 14, wherein the metal nanostructure comprises a metal selected from the group consisting of gold, silver, or a combination thereof.

17. The nanoparticle diamond-metal conjugate of claim 14, wherein the metal nanostructure comprises a magnetic layer.

18. The nanoparticle diamond-metal conjugate of claim 17, wherein the metal nanostructure comprises a metal selected from the group consisting of nickel, cobalt, iron, or chemical compounds thereof.

19. The nanoparticle diamond-metal conjugate of claim 1, wherein being at least partially directly attached comprises the diamond nanoparticle being wholly directly attached to the layer of the metallic nanostructure.

* * * * *